United States Patent
Nakamichi et al.

[11] Patent Number: 5,837,285
[45] Date of Patent: Nov. 17, 1998

[54] FAST SOLUBLE TABLET

[76] Inventors: Kouichi Nakamichi, 13-16, Kitayamadai 1-chome, Koseicho, Koga-gun Shiga 520-32, Japan; Shogo Izumi, 3-94, Nishitsutsujigaoka Miyamadai 1-chome, Kameoka-shi Kyoto 621, Japan; Hiroyuki Yasuura, 10-20-312, Hirai 5-chome, Kusatsu-shi, Shiga 525, Japan

[21] Appl. No.: 290,890

[22] PCT Filed: Feb. 17, 1993

[86] PCT No.: PCT/JP93/00192

§ 371 Date: Aug. 18, 1994

§ 102(e) Date: Aug. 18, 1994

[87] PCT Pub. No.: WO93/15724

PCT Pub. Date: Aug. 19, 1993

[30] Foreign Application Priority Data

Feb. 18, 1992 [JP] Japan .................................. 4-069565

[51] Int. Cl.⁶ .................................................. A61K 9/20
[52] U.S. Cl. .................. 424/464; 424/435; 424/465; 424/474; 424/479; 424/480; 424/482
[58] Field of Search .................... 424/464, 465, 424/435, 479, 474, 480, 482

[56] References Cited

U.S. PATENT DOCUMENTS

| | | | |
|---|---|---|---|
| 5,073,374 | 12/1991 | McCarty | 424/435 |
| 5,073,380 | 12/1991 | Babu et al. | 424/472 |
| 5,082,667 | 1/1992 | Van Scoik | 424/469 |
| 5,112,616 | 5/1992 | McCarty | 424/435 |
| 5,234,696 | 8/1993 | Van Scoik et al. | 424/489 |
| 5,288,501 | 2/1994 | Nürnberg et al. | 424/465 |
| 5,501,861 | 3/1996 | Makino et al. | 424/464 |

FOREIGN PATENT DOCUMENTS

| | | |
|---|---|---|
| 42808/85 | 12/1985 | Australia . |
| 0371466 | 6/1990 | European Pat. Off. . |
| 53-44618 | 4/1978 | Japan . |
| 61-205208 | 9/1986 | Japan . |

*Primary Examiner*—Thurman K. Page
*Assistant Examiner*—Sharon Howard
*Attorney, Agent, or Firm*—Graham & James LLP

[57] ABSTRACT

The object of the present invention is to provide a tablet that dissolves rapidly in the oral cavity (fast soluble tablets) that can be produced by a simple method without special preparation technology. The present invention is a fast soluble tablet which comprises two features: ① the tablet base component is a sugar alcohol or the like, and ② a kneaded mixture of a drug and a sugar alcohol or the like is subjected to compressive shaping prior to drying in the process when compressive shaped for preparing tablets by wet granulation. The fast soluble tablet of the present invention can be produced by a modification of the conventional tableting method, and possesses sufficient physico-chemical stability.

28 Claims, 2 Drawing Sheets

FAST SOLUBLE TABLET

TECHNICAL FIELD

The present invention relates to a drug-containing fast soluble tablet that dissolves rapidly in the oral cavity.

The fast soluble tablet usually dissolves in the oral cavity within 15 seconds to 3 minutes, and is suitable for administration to infants, the aged, severely affected patients and others who have difficulty in taking tablets.

BACKGROUND ART

Oral dosage forms of drugs include tablets, granules, powders and liquids. Liquids, such as syrups, are suitable for administration to the physically weakened aged and infants because they are easily swallowable. However, they are not convenient because they must be accurately weighed for each use. Another drawback is that the tendency to deteriorate easily upon exposure to heat or atmosphere degrades the drug's chemical and physical stability.

Granules and powders are free of the above drawbacks, but they are not easily swallowable, and taking the accurate dose is difficult unless they are taken with water etc.

Tablets are suitable for administration of a certain accurate volumes and offers excellent chemical and physical stability for the drug contained, but they have a drawback of difficult swallow for infants, the aged, severely affected patients and others. Overcoming the drawback of poor swallowability would make it possible to provide an excellent preparation free of the above-described drawbacks in other dosage forms.

As a solution to the problem of poor swallowability in tablets, freeze-dried preparations in a tablet form, based on a water-soluble polymer, have recently been developed (e.g., Japanese Patent Unexamined Publication Nos. 44619/1978 and 86837/1991). They have overcome the drawback of poor swallowability in tablets by causing the preparation to dissolve rapidly in the oral cavity. However, they require a special preparation technology known as freeze-drying, resulting in drawbacks such as difficulty in industrial mass-production, high production cost and poor physical stability.

In recent years, tablets have been produced by subjecting tablet components to compressive shaping under high pressure in a dry state. This is because tablets are essentially intended to be disintegrated in the gastrointestinal tract to cause drug absorption and must be physically and chemically stable from completion of tableting to reach to the gastrointestinal tract, so that the tablet components must be strongly bound together by a compressive pressure. In early times, wet tablets were available, which were molded and shaped into tablets while in a wet state, followed by drying. However, such tablets were not rapidly soluble in the oral cavity because they were intended to be disintegrated in the gastrointestinal tract. Also, as these tablets are not strongly compressed mechanically and lack shape retention, they are not practically applicable to modern use.

DISCLOSURE OF THE INVENTION

The object of the present invention is to provide a fast soluble tablet that can be produced by a simple method without the above-described special preparation technology known as freeze-drying.

Through intensive investigation, the present inventors found that the above object could be accomplished by producing tablets based on a pharmaceutical additive rapidly soluble in water by a modification of the conventional tableting method based on wet granulation and completed the present invention.

A gist of the present invention is characterized by two features: 1) the tablet base component is a pharmaceutical additive rapidly soluble in water, and 2) a kneaded mixture of a drug and a pharmaceutical additive rapidly soluble in water is subjected to compressive shaping while in a wet state.

Figure 1:
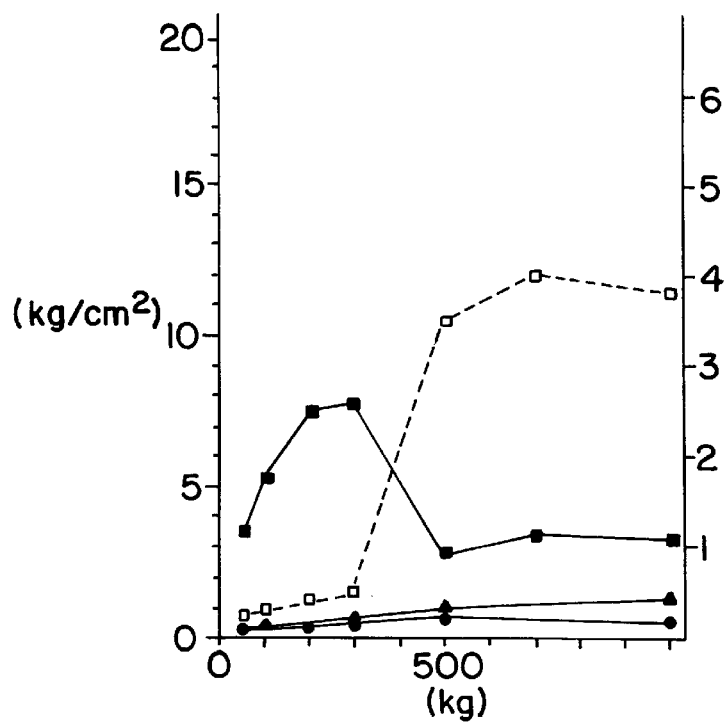
FIGS. 1–4 show the relationship between tensile strength, oral cavity, dissolution time and compression force for the inventive tablets.

The present invention is hereinafter described in detail.

The pharmaceutical additive rapidly soluble in water may be any water-soluble crystalline or powdery solid, exemplified by substances in common use as excipients. It is preferable, however, that the pharmaceutical additive is a sweetening substance, since the fast soluble tablet of the present invention dissolves rapidly in the oral cavity. Such substances include succharides such as sucrose, lactose, glucose and fructose, and sugar alcohols such as xylitol, sorbitol and mannitol.

Of the above-mentioned sugar alcohols, xylitol is preferred because it has a good taste and dissolves most rapidly in the oral cavity. Mannitol and lactose are excellent in the compressive property described later, although they are inferior to xylitol in taste and dissolution rate.

In the present invention, these substances may be used in combination. Appropriate combination can offer only a combination of advantages thereof.

The fast soluble tablet relating to the present invention is produced by subjecting a kneaded mixture of a pharmaceutical additive rapidly soluble in water as described above and a drug to compressive shaping before drying when compressive shaping is performed in the conventional tableting method based on wet granulation. The present tablets are different from conventional tablets in that the shaping and drying operations are reversed in order; conventional tablets are produced by mixing starting materials, adding a binder, kneading and drying the mixture and subjecting the mixture to compressive shaping.

The compressive shaping pressure for shaping the fast soluble tablet relating to the present invention may be relatively low, e.g., 50–1,000 kg is sufficient. Although decreasing the pressure tends to yield tablets of shorter oral cavity dissolution time, compressive shaping pressures lower than 50 kg result in formation of practically unapplicable tablets with insufficient tensile strength. Although increasing the pressure tends to yield more tough tablets of improved tensile strength, compressive shaping pressures exceeding 1,000 kg usually result in formation of tablets of longer oral cavity dissolution time. In some cases, however, tablets with practically acceptable strength are obtained from an appropriate combination of two or more of the pharmaceutical additives, even when the compressive shaping pressure is lower than 50 kg. Also, in some cases tablets with shorter oral cavity dissolution time may be obtained from an appropriate combination of two or more of the pharmaceutical additives, even when the compressive shaping pressure exceeds 1,000 kg. Fast soluble tablets produced under a compressive shaping pressure out of the range of 50–1,000 kg are therefore included in the scope of the present invention.

Tablets whose tensile strength exceeds 5 $kg/cm^2$ are practically applicable. In some cases, however, tablets with even lower tensile strength are practically applicable if they are packaged in suitable forms.

The mechanical strength of the fast soluble tablet relating to the present invention is retained mainly by the crosslinking force of the pharmaceutical additive rapidly soluble in water.

Conventional tablets are produced under compressive shaping pressures of about 500–3,000 kg.

When a sugar alcohol is applied in the present invention, e.g., xylitol is used alone, it is preferable that the compressive shaping pressure is about 50–300 kg. Lower compressive shaping pressures make tablet shaping difficult. Higher compressive shaping pressures result in formation of practically unapplicable tablets of insufficient tensile strength (see FIG. 1).

When xylitol alone is used as a sugar alcohol, compressive shaping pressures exceeding 300 kg result in formation of tablets with decreased tensile strength and increased oral cavity dissolution time. When xylitol is used in a mixture with lactose, mannitol or the like, tablets with sufficiently high tensile strength and short oral cavity dissolution time can be obtained even when the compressive shaping pressure exceeds 300 kg.

Figure 2:
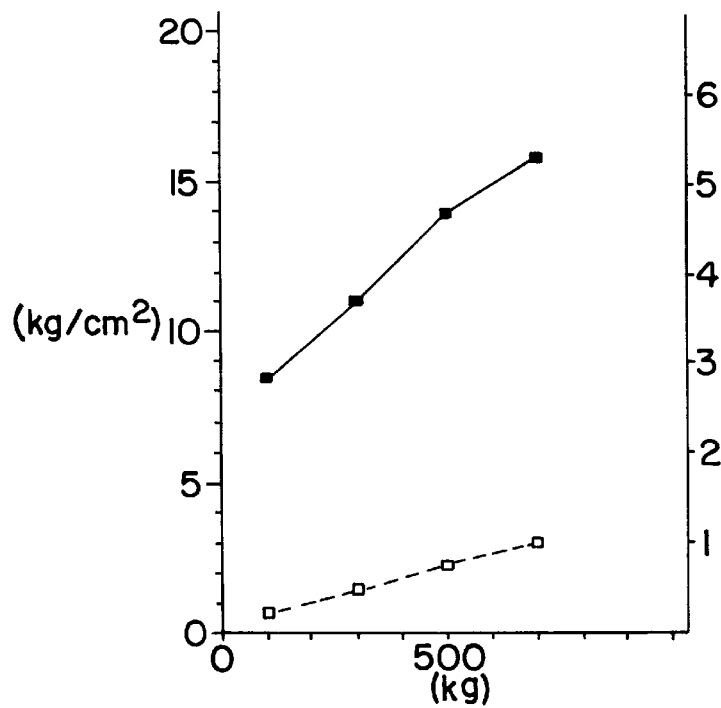

For example, when xylitol is used in combination with lactose, tablets with shorter oral cavity dissolution time and sufficient tensile strength can be obtained by mixing them in a ratio of, for example, 8:2 (see FIG. 2).

Figure 3:
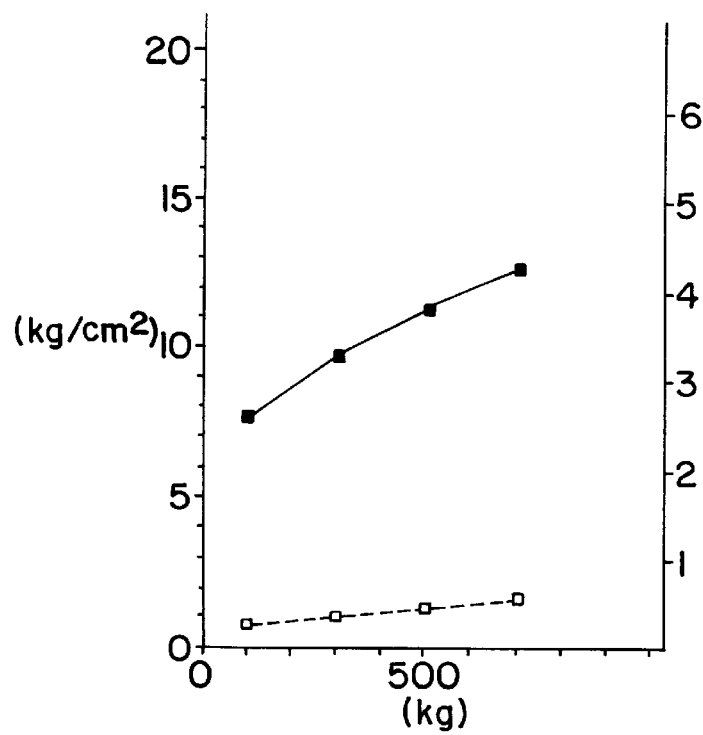

For example, when xylitol is used in combination with mannitol, tablets with shorter oral cavity dissolution time and sufficient tensile strength can be obtained by mixing them in a ratio of, for example, 8:2 (see FIG. 3).

As mentioned above, when xylitol is used in a mixture with lactose or mannitol, better results are obtained than those obtained with xylitol alone. These results, however, have not been expected from the results with mannitol alone or lactose alone. This is because using mannitol alone or lactose alone results in considerably increased oral cavity dissolution time as well as increased tensile strength when the compressive shaping pressure exceeds 300 kg (see FIG. 4).

The fast soluble tablet relating to the present invention is characterized by rapid dissolution in the oral cavity. For example, when it is intended to incorporate a drug which may cause a problem, if used as such, e.g., a drug which has a high bitterness, a masking treatment such as microcapsulation or crystal surface coating is performed as appropriate, after which the drug is incorporated in the fast soluble tablet of the present invention, result in elimination of such problem.

The kneaded mixture of a drug and a pharmaceutical additive rapidly soluble in water is usually prepared by mixing the pharmaceutical additive rapidly soluble in water and the appropriately treated drug, adding and uniformly dispersing water, a binder solution or a saturated sugar solution, and kneading. The amount of water added is preferably about 1–10% by weight, most preferably about 3% by weight, in the tablet composition before compressive shaping. Excess water results in dissolution of sugar alcohol or sugar, or decreased shape retention, which in turn adversely affect the compressive shaping that follows and make it difficult to dry the shaped product. Insufficient water results in tableting failures such as cracking at shaping, thus hampering preferred embodiment. The shaped tablet, even if obtained, lacks mechanical strength, and is fragile. The water added is preferably purified water, for instance.

Compressive shaping can be achieved, irrespective of the form of the kneaded mixture, whether particulate, granular, soft lumpy or the like, as long as the kneaded mixture of the drug and the pharmaceutical additive rapidly soluble in water is wet. Compressive shaping machines which can be used include ordinary tableting machines, automatic compressive shaping machines for Japanese cakes and lump sugar machines.

The fast soluble tablet relating to the present invention can be produced more simply and in larger amounts, in comparison with the above-described tableting method using freeze-drying technique, because they can be produced by a modification of the conventional tableting method based on wet granulation compression, as stated above.

In the present invention, to further improve the physical properties of the preparation, known binders may be added in the process of the kneading operation. Although the binder for the present invention is not subject to limitation, preference is given to substances of relatively high dissolution rate. Such binders include polyvinylpyrrolidone (PVP), hydroxypropyl cellulose (HPC) and hydroxypropyl methylcellulose (HPMC) and the like. Acacia etc. may also be incorporated as appropriate.

The binder for the present invention may be contained at 0.1 to several percent by weight, preferably about 0.5–1% by weight, in the tablet composition before compressive shaping.

The fast soluble tablet relating to the present invention may be glazed by steam exposure for one to several seconds after compressive shaping and drying, to smooth the tablet surface for good appearance and prevent abrasion of the tablet surface.

Any drug is applicable to the fast soluble tablet relating to the present invention, as long as it is orally administered. Such drugs include the following:

1. Antipyretic Analgesic Anti-inflammatory Agents

Indomethacin, aspirin, diclofenac sodium, ketoprofen, ibuprofen, mefenamic acid, dexamethasone, dexamethasone sodium sulfate, hydrocortisone, prednisolone, azulene, phenacetin, isopropylantipyrin, acetaminophen, benzydamine hydrochloride, phenylbutazone, flufenamic acid, mefenamic acid, sodium salicylate, choline salicylate, sasapyrine, clofezone, etodolac.

2. Antiulcer Agents

Sulpiride, cetraxate hydrochloride, gefarnate, irsogladine maleate, cimetidine, lanitidine hydrochloride, famotidine, nizatidine, roxatidine acetate hydrochloride.

3. Coronary Vasodilators

Nifedipine, isosorbide dinitrate, diltiazem hydrochloride, trapidil, dipyridamole, dilazep dihydrochloride, methyl 2,6-dimethyl-4-(2-nitrophenyl)-5-(2-oxo-1,3,2-dioxaphosphorinan-2-yl)-1,4-dihydropyridine-3-carboxylate, verapamil, nicardipine, nicardipine hydrochloride, verapamil hydrochloride.

4. Peripheral Vasodilators

Ifenprodil tartrate, cinepazide maleate, cyclandelate, cinnarizine, pentoxyfyline.

5. Antibiotics

Ampicillin, amoxicillin, cefalexin, erythromycin ethylsuccinate, bacampicillin hydrochloride, minocycline hydrochloride, chloramphenicol, tetracycline, erythromycin.

6. Synthetic Antibacterial Agents

Nalidixic acid, piromidic acid, pipemidic acid trihydrate, enoxacin, cinoxacin, ofloxacin, norfloxacin, ciprofloxacin hydrochloride, sulfamethoxazole trimethoprim, 6-fluoro-1-methyl-7-[4-(5-methyl-2-oxo-1,3-dioxolen-4-yl)methyl-1-piperazinyl]-4-oxo-4H [1,3]thiazeto[3,2-a]quinoline-3-carboxylic acid.

7. Antispasmodics

Propantheline bromide, atropine sulfate, oxapium bromide, timepidium bromide, butylscopolamine bromide, trospium chloride, butropium bromide, N-methylscopolamine methylsulfate, methyloctatropine bromide, butropium bromide.

8. Antitussive, Anti-asthmatic Agents

Theophylline, aminophylline, methylephedrine hydrochloride, procaterol hydrochloride, trimetoquinol hydrochloride, codeine phosphate, sodium cromoglicate, tranilast, dextromethorphane hydrobromide, dimemorfan phosphate, clobutinol hydrochloride, fominoben hydrochloride, benproperine phosphate, tipepidine hibenzate, eprazinone hydrochloride, clofedanol hydrochloride, ephedrine hydrochloride, noscapine, calbetapentane citrate, oxeladin tannate, isoaminile citrate.

9. Bronchodilators

Diprophylline, salbutamol sulfate, clorprenaline hydrochloride, formoterol fumarate, orciprenalin sulfate, pirbuterol hydrochloride, hexoprenaline sulfate, bitolterol mesylate, clenbuterol hydrochloride, terbutaline sulfate, mabuterol hydrochloride, fenoterol hydrobromide, methoxyphenamine hydrochloride.

10. Diuretics

Furosemide, acetazolarmide, trichlormethiazide, methyclothiazide, hydrochlorothiazide, hydroflumethiazide, ethiazide, cyclopenthiazide, spironolactone, triamterene, fluorothiazide, piretanide, metruside, ethacrynic acid, azosemide, clofenamide.

11. Muscle Relaxants

Chlorphenesin carbamate, tolperisone hydrochloride, eperisone hydrochloride, tizanidine hydrochloride, mephenesin, chlorozoxazone, phenprobamate, methocarbamol, chlormezanone, pridinol mesylate, afloqualone, baclofen, dantrolene sodium.

12. Brain Metabolism Improvers

Meclofenoxate hydrochloride.

13. Minor Tranquilizers

Oxazolam, diazepam, clotiazepam, medazepam, temazepam, fludiazepam, meprobamate, nitrazepam, chlordiazepoxide.

14. Major Tranquilizers

Sulpirid, clocapramine hydrochloride, zotepine, chlorpromazinon, haloperidol.

15. β-Blockers

Pindolol, propranolol hydrochloride, carteolol hydrochloride, metoprolol tartrate, labetalol hydrochloride, acebutolol hydrochloride, butetolol hydrochloride, alprenolol hydrochloride, arotinolol hydrochloride, oxprenolol hydrochloride, nadolol, bucumolol hydrochloride, indenolol hydrochloride, timolol maleate, befunolol hydrochloride, bupranolol hydrochloride.

16. Antiarrhythmic Agents

Procainamide hydrochloride, disopyramide, ajimaline, quinidine sulfate, aprindine hydrochloride, propafenone hydrochloride, mexiletine hydrochloride.

17. Gout Suppressants

Allopurinol, probenecid, colchicine, sulfinpyrazone, benzbromarone, bucolome.

18. Anticoagulants

Ticlopidine hydrochloride, dicumarol, warfarin potassium.

19. Antiepileptic Agents

Phenytoin, sodium valproate, metharbital, carbamazepine.

20. Antihistaminics

Chlorpheniramine maleate, cremastin fumarate, mequitazine, alimemazine tartrate, cycloheptazine hydrochloride.

21. Antiemetics

Difenidol hydrochloride, metoclopramide, domperidone, betahistine mesylate, trimebutine maleate.

22. Hypotensives

Dimethylaminoethyl reserpilinate dihydrochloride, rescinnamine, methyldopa, prazosin hydrochloride, bunazosin hydrochloride, clonidine hydrochloride, budralazine, urapidin.

23. Sympathomimetic Agents

Dihydroergotamine mesylate, isoproterenol hydrochloride, etilefrine hydrochloride.

24. Expectorants

Bromhexine hydrochloride, carbocysteine, ethyl cysteine hydrochloride, methyl cysteine hydrochloride.

25. Oral Antidiabetic Agents

Glibenclamide, tolbutamide, glymidine sodium.

26. Circulatory Agents

Ubidecarenone, ATP-2Na.

27. Iron Preparations

Ferrous sulfate, dried ferrous sulfate.

28. Vitamins

Vitamin B1, vitamin B2, vitamin B6, vitamin B12, vitamin C, folic acid.

29. Pollakiuria Remedies

Flavoxate hydrochloride, oxybutynin hydrochloride, terodiline hydrochloride, 4-diethylamino-1,1-dimethyl-2-butynyl (±)-α-cyclohexyl-α-phenylglycolate hydrochloride monohydrate.

30. Angiotensin-converting enzyme inhibitors

Enalapril maleate, alacepril, delapril hydrochloride.

EFFECTS OF THE INVENTION

The fast soluble tablet relating to the present invention has the following effects:

(1) Offers improved compliance, including safe administration to the aged, children, infants and patients weak in swallowing ability.

(2) Free of the risk of suffocation due to a physical obstruction when swallowed, thus offering improved safety.

(3) Safely administrable to patients on water intake restriction.

(4) Easily portable and suitable for transportation by patients.

(5) Free of the need of weighing, an essential drawback in liquids etc.

(6) Drug retention at high concentrations in tablets allows application to drugs that must be administered at high doses.

(7) Can be industrially produced more simply, more efficiently and in larger amounts, in comparison with tableting based on freeze-drying.

BEST MODES FOR CARRYING OUT THE INVENTION

The present invention is hereinafter illustrated in more detail by means of the following examples.

EXAMPLE 1

To 60 g of xylitol, 2 ml of purified water was added, followed by kneading in a mortar. 1 g of the kneaded mixture was subjected to compressive shaping at a compression force of 100–700 kg and a compression rate of 20 mm/min, using a material testing machine (Autograph (trade mark) :AG-5000, produced by Shimadzu Corporation), to yield tablets of 13 mm diameter. The resulting tablets were dried at 50° C. for 2 hours in a hot air circulation oven (GT-100, produced by Alp Corporation) to yield fast soluble tablets of the present invention.

EXAMPLE 2

48 g of xylitol and 12 g of lactose were uniformly mixed in a mortar, followed by kneading with 2 ml of purified water added. 1 g of the kneaded mixture was subjected to compressive shaping at a compression force of 100–700 kg and a compression rate of 20 mm/min, using a material testing machine (Autograph (trade mark):AG-5000, produced by Shimadzu Corporation), to yield tablets of 13 mm diameter. The resulting tablets were dried at 50° C. for 2 hours in a hot air circulation oven (GT-100, produced by Alp Corporation) to yield fast soluble tablets of the present invention.

EXAMPLE 3

48 g of xylitol and 12 g of mannitol were uniformly mixed in a mortar, followed by kneading with 2 ml of purified water added. 1 g of the kneaded mixture was subjected to compressive shaping at a compression force of 100–700 kg and a compression rate of 20 mm/min, using a material testing machine (Autograph (trade mark):AG-5000, produced by Shimadzu Corporation), to yield tablets of 13 mm diameter. The resulting tablets were dried at 50° C. for 2 hours in a hot air circulation oven (GT-100, produced by Alp Corporation) to yield fast soluble tablets of the present invention.

EXAMPLE 4

60 g of mannitol was placed in a mortar and kneaded with 2 ml of purified water. 1 g of the kneaded mixture was subjected to compressive shaping at a compression force of 100–700 kg and a compression rate of 20 mm/min, using a material testing machine (Autograph (trade mark):AG-5000, produced by Shimadzu Corporation), to yield tablets of 13 mm diameter. The resulting tablets were dried at 50° C. for 2 hours in a hot air circulation oven (GT-100, produced by Alp Corporation) to yield fast soluble tablets of the present invention.

EXAMPLE 5

308 g of xylitol, 77 g of mannitol, 12.5 g of diclofenac sodium and 2.5 g of polyvinylpyrrolidone were mixed in a kneader (KM-1.5, produced by Kikusui Seisakusho, Ltd.) for 10 minutes, followed by kneading with 12 ml of purified water added. The resulting mixture was applied to a feather mill (FM-1, produced by Hosokawa Micron Corp.) equipped with a screen of 12 mm pores, to uniformize particle size. The resulting granules were subjected to compressive shaping at a compression force of 200 kg, using a tableting machine (Clean Press Correct 12HUK, produced by Kikusui Seisakusho, Ltd.) equipped with a forced mechanical stirrer, to yield tablets of 10.5 mm diameter weighing 800 mg each. The shaped tablets were then dried at 50° C. for 3 hours in a hot air circulation oven (GT-100, produced by Alp Corporation) to yield fast soluble tablets of the present invention.

EXAMPLE 6

3 g of polyvinylpyrrolidone, 100 g of lactose and 3 g of oxybutynin hydrochloride were mixed in a micro-type through-vision mixer (W-8, produced by Tsutsui Rikagaku Kiki) for 8 minutes. 106 g of this mixture and 394 g of xylitol were mixed in a kneader (KM-1.5, produced by Kikusui Seisakusho, Ltd.) for 10 minutes, followed by kneading with 15 ml of purified water added. The resulting mixture was applied to a feather mill (FM-1, produced by Hosokawa Micron Corp.) equipped with a screen of 12 mm pores, to uniformize particle size. The resulting granules were subjected to compressive shaping at a compression force of 150 kg, using a tableting machine (Clean Press Correct 12HUK, produced by Kikusui Seisakusho, Ltd.) equipped with a forced mechanical stirrer, to yield tablets of 9 mm diameter weighing 500 mg each. The shaped tablets were then dried at 55° C. for 3 hours in a hot air circulation oven (GT-100, produced by Alp Corporation) to yield fast soluble tablets of the present invention.

EXAMPLE 7

2.5 g of acacia powder, 146 g of mannitol and 10 g of nifedipine were mixed in a micro-type through-vision mixer (W-8, produced by Tsutsui Rikagaku Kiki) for 8 minutes. 158.5 g of this mixture and 341.5 g of xylitol were mixed in a kneader (KM-1.5, produced by Kikusui Seisakusho, Ltd.) for 10 minutes, followed by kneading with 14 ml of purified water added. The resulting mixture was applied to a feather mill (FM-1, produced by Hosokawa Micron Corp.) equipped with a screen of 12 mm pores, to uniformize particle size. The resulting granules were subjected to compressive shaping at a compression force of 220 kg, using a rotary tableting machine (RT-F-9, produced by Kikusui Seisakusho, Ltd.), to yield tablets of 15 mm diameter weighing 1,000 mg each. The shaped tablets were then dried at 55° C. for 3 hours in a hot air circulation oven (GT-100, produced by Alp Corporation) to yield fast soluble tablets of the present invention.

EXAMPLE 8

1.5 g of polyvinylpyrrolidone, 412.5 g of xylitol, 111 g of lactose and 125 g of cefalexin were mixed in a kneader (KM-1.5, produced by Kikusui Seisakusho, Ltd.) for 10 minutes, followed by kneading with 20 ml of purified water added. The resulting mixture was applied to a feather mill (FM-1, produced by Hosokawa Micron Corp.) equipped with a screen of 12 mm pores, to uniformize particle size. The resulting granules were subjected to compressive shaping at a compression force of 180 kg, using a rotary tableting machine (RT-F-9, produced by Kikusui Seisakusho, Ltd.), to yield tablets of 15 mm diameter weighing 1,300 mg each. The shaped tablets were then dried at 55° C. for 3 hours in a hot air circulation oven (GT-100, produced by Alp Corporation) to yield fast soluble tablets of the present invention.

Comparative Example 1

300 g of xylitol was passed through a 32-mesh sieve. 1 g of the powder was subjected to compressive shaping at a compression force of 50–1,000 kg and a compression rate of 20 mm/min, using a material testing machine (Autograph (trade mark):AG-5000, produced by Shimadzu Corporation), to yield tablets of 13 mm diameter for comparative testing.

Comparative Example 2

300 g of mannitol was passed through a 32-mesh sieve. 1 g of the powder was subjected to compressive shaping at a compression force of 100–700 kg and a compression rate of 20 mm/min, using a material testing machine (Autograph (trade mark):AG-5000, produced by Shimadzu Corporation), to yield tablets of 13 mm diameter for comparative testing.

Test Example 1

For the inventive fast soluble tablets of Example 1, the tablets of Comparative Example 1, and the undried tablets of Example 1, tensile strength and oral cavity dissolution time were measured. Tensile strength was measured using a material testing machine (Autograph (trade mark):AG-5000, produced by Shimadzu Corporation) equipped with a 100 KGF load cell, at a compression rate of 20 mm/min, with a full scale of 10–20 KGF. The point at which the load reduction rate for 1 second lowerd to 50% of the full scale was taken as the breaking point. On the basis of breaking point data, the tensile strength of each tablet preparation was calculated as the mean of 5 tablets using the following equation:

$\tau = 2P/\pi DT$ $\tau$: Tensile strength (kg/cm$^2$)

P: Hardness (kg)

D: Tablet diameter (cm)

T: Tablet thickness (cm)

Oral cavity dissolution time was measured as the mean of 5 subjects. Each tablet was kept unbitten in the mouth, and the time to tablet mass dissolution and disappearance was measured. The results are given in FIG. 1.

From FIG. 1, it is seen that the fast soluble tablet of the present invention had excellent properties for a fast soluble tablet, having a tensile strength exceeding 3 kg/cm$^2$ and an oral cavity dissolution time within 30 second when it was prepared under a compression force of 50–300 kg. As for the undried tablets and the tablets obtained by dry tableting, tensile strength was lower than 3 kg/cm$^2$ when they were prepared under a compression force of 50–1,000 kg; they were not practically applicable.

Test Example 2

For the inventive fast soluble tablets of Example 2, tensile strength and oral cavity dissolution time were measured in the same manner as in Test Example 1. The results are given in FIG. 2.

From FIG. 2, it is seen that the fast soluble tablet of the present invention has excellent properties for a fast soluble tablet, having a tensile strength exceeding 8 kg/cm$^2$ and an oral cavity dissolution time within 1 minute over the range of compression forces measured.

Test Example 3

For the inventive fast soluble tablets of Example 3, tensile strength and oral cavity dissolution time were measured in the same manner as in Test Example 1. The results are given in FIG. 3.

From FIG. 3, it is seen that the fast soluble tablet of the present invention had excellent properties for a fast soluble tablet, having a tensile strength exceeding 7 kg/cm$^2$ and an oral cavity dissolution time within 40 seconds over the range of compression forces measured.

Test Example 4

For the inventive fast soluble tablets of Example 4, the tablets of Comparative Example 2 and the undried tablets of Example 4, tensile strength and oral cavity dissolution time were measured in the same manner as in Test Example 1. The results are given in FIG. 4.

Figure 4:
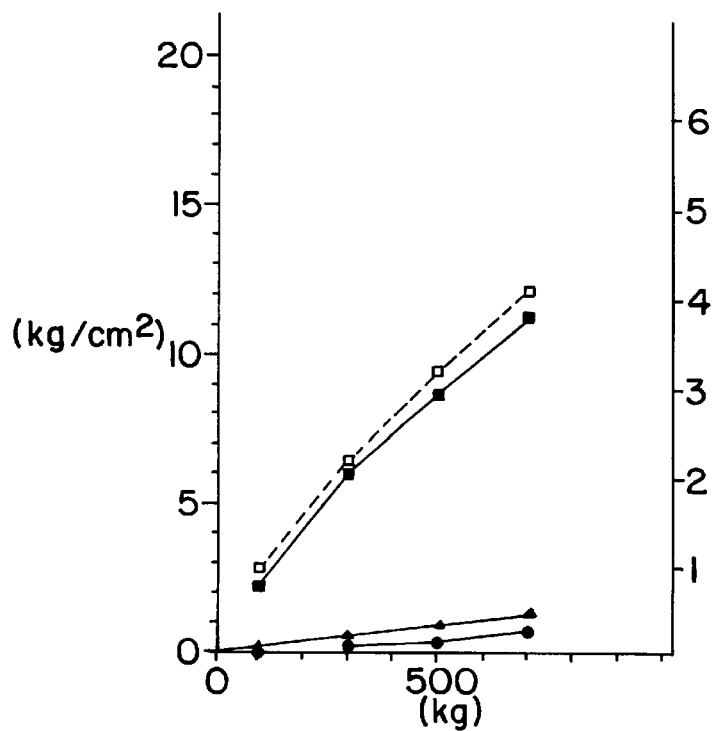

From FIG. 4, it is seen that the fast soluble tablet of the present invention were practically applicable, having much higher tensile strength, in comparison with the undried tablets and the tablets obtained by dry tableting.

Test Example 5

For the inventive fast soluble tablets of Examples 5 through 8, tensile strength, oral cavity dissolution time, disintegration time and degree of wear were measured. Tensile strength and oral cavity dissolution time were measured in the same manner as in Test Example 1. Disintegration time was measured by the method using water specified in the Pharmacopoeia of Japan. Friability was measured on one tablet for each preparation, using a friabilator. The results are given in Table 1.

TABLE 1

| | Example 5 | Example 6 | Example 7 | Example 8 |
|---|---|---|---|---|
| Tensile strength (kg/cm$^2$) | 9.1 | 7.5 | 12.2 | 8.5 |
| Dissolution time (in oral cavity, seconds) | 15 | 15 | 18 | 25 |
| Disintegration time (seconds) | 12 | 12 | 15 | 20 |
| Friability (%) (in 3 minutes) | 0.3 | 0.1 | 0.2 | 0.3 |
| Remarks | *Good appearance *Dissolved rapidly in the oral cavity. *Easily swallowable. | *Good appearance *Dissolved rapidly in the oral cavity. *Easily swallowable. | *Good appearance *Dissolved rapidly in the oral cavity. *Easily swallowable. | *Good appearance *Dissolved rapidly in the oral cavity. *Easily swallowable. |

From Table 1, it is seen that the fast soluble tablets of the present invention had excellent properties for a fast soluble tablet, having a tensile strength exceeding 7 kg/cm$^2$ and an oral cavity dissolution time within 30 seconds.

FIG. 1 shows the relations between tensile strength, and oral cavity dissolution time and compression force for each of the inventive fast soluble tablets of Example 1, the tablets of Comparative Example 1, and the undried tablets of Example 1.

The abscissa indicates compression force; the left ordinate indicates tensile strength (kg/cm$^2$); the right ordinate indicates oral cavity dissolution time (min).

In Figure, the symbols denote the following:

—■—: Tensile strength of the inventive fast soluble tablets of Example 1

—□—: Oral cavity dissolution time of the inventive fast soluble tablets of Example 1

—▲—: Tensile strength of the undried tablets of Example 1

—●—: Tensile strength of the tablets of Comparative Example 1

FIG. 2 shows the relations between tensile strength, and oral cavity dissolution time and compression force for the inventive fast soluble tablets of Example 2.

The abscissa indicates compression force; the left ordinate indicates tensile strength (kg/cm$^2$); the right ordinate indicates oral cavity dissolution time (min).

In Figure, the symbols denote the following:

—■—: Tensile strength of the inventive fast soluble tablets of Example 2

—□—: Oral cavity dissolution time of the inventive fast soluble tablets of Example 2

FIG. 3 shows the relations between tensile strength, and oral cavity dissolution time and compression force for the inventive fast soluble tablets of Example 3.

The abscissa indicates compression force; the left ordinate indicates tensile strength ($kg/cm^2$); the right ordinate indicates oral cavity dissolution time (min).

In Figure, the symbols denote the following:

—■—: Tensile strength of the inventive fast soluble tablets of Example 3

—□—: Oral cavity dissolution time of the inventive fast soluble tablets of Example 3

FIG. 4 shows the relations between tensile strength, and oral cavity dissolution time and compression force for each of the inventive fast soluble tablets of Example 4, the tablets of Comparative Example 2, and the undried tablets of Example 4.

The abscissa indicates compression force; the left ordinate indicates tensile strength ($kg/cm^2$); the right ordinate indicates oral cavity dissolution time (min).

In Figure, the symbols denote the following:

—■—: Tensile strength of the inventive fast soluble tablets of Example 4

—□—: Oral cavity dissolution time of the inventive fast soluble tablets of Example 4

—▲—: Tensile strength of the undried tablets of Example 4

—●—: Tensile strength of the tablets of Comparative Example 2

What is claimed is:

1. A rapidly soluble tablet for oral administration of a therapeutic substance to a human or animal which comprises a kneaded wet compressed shaped tablet which comprises an amount of xylitol and at least one member selected from the group consisting of lactose and mannitol sufficient to form a rapidly soluble tablet, in combination with a therapeutically effective amount of a therapeutic substance, said tablet having been compression shaped with a compression force of from about 50 to about 1000 kg in a wet state and thereafter dried, said wet tablet containing from about 1 to about 10% by weight of water.

2. A tablet according to claim 1 wherein the additive is a water-soluble crystalline or powdery solid.

3. A tablet according to claim 1 wherein the additive is a sweetening substance.

4. A tablet according to claim 3 wherein the sweetening substance is a saccharide, a sugar alcohol or a mixture thereof.

5. A tablet according to claim 1 wherein the additive is xylitol, manitol, lactose or a mixture of two or three thereof.

6. A tablet according to claim 1 wherein the therapeutic substance is subjected to a masking treatment prior to combination with the additive.

7. A tablet according to claim 1 which further comprises a binder.

8. A tablet according to claim 7 wherein the binder is polyvinylpyrrolidone, hydroxypropyl cellulose, hydroxypropyl methylcellulose or acacia.

9. A tablet according to claim 1 wherein the therapeutic substance is an antipyretic, an analgesic, an antiinflammatory agent, an antiulcer agent, a coronary vasodilator, a peripheral vasodilator, an antibiotic, an antibacterial agent, an antispasmodic, an antitussive, an antiasthmatic agent, a bronchodilator, a diuretic, a muscle relaxant, a brain metabolism improver, a tranquilizer, a β-blocker, an antiarrhythmic agent, a gout suppressant, an anticoagulant, an antiepileptic agent, an antihistaminic, an antiemetic, a hypotensive, a sympathomimetic agent, an expectorant, an oral antidiabetic agent, a circulatory agent, an iron preparation, a vitamin, a pollakiuria remedy, or an angiotensin-converting enzyme inhibitor.

10. A process for the production of a rapidly soluble tablet for oral administration of a therapeutic substance to a human or animal which comprises mixing a pharmaceutical additive which is rapidly soluble in water and a therapeutically effective amount of a therapeutic substance, adding and uniformly dispersing an amount of water of from about 1 to about 10% by weight of the wet tablet and sufficient to enable the mixture to be kneaded, kneading the mixture and while the kneaded mixture is wet, compression shaping it with an automatic compressive cake shaping machine or a lump sugar machine at a compression force of about 50 to about 1000 kg into tablet form, and drying the tablet, whereby the tablets produced are rapidly soluble in the oral cavity of a human or animal upon administration.

11. A process according to claim 10 wherein the amount of water is about 3 percent by weight.

12. A process according to claim 10 which further comprises mixing a binder, of about 0.1 percent to about 2 percent by weight of the tablet before compression shaping, with the additive and the therapeutic substance.

13. A process according to claim 7 wherein the binder is polyvinylpyrrolidone, hydroxypropyl cellulose, hydroxypropyl methylcellulose or acacia.

14. A process according to claim 10 wherein the therapeutic substance is subjected to a masking treatment prior to being mixed with the pharmaceutical additive.

15. A process according to claim 12 wherein the amount of binder is from about 0.5 to about 1 percent by weight.

16. A process according to claim 10 wherein the additive is a water-soluble crystalline or powdery solid.

17. A process according to claim 10 wherein the additive is a sweetening substance.

18. A process according to claim 17 wherein the sweetening substance is a saccharide, a sugar alcohol or a mixture thereof.

19. A process according to claim 10 wherein the additive is xylitol, mannitol, lactose or a mixture of two or three thereof.

20. A process according to claim 10 wherein the therapeutic substance is an antipyretic, an analgesic, an antiinflammatory agent, an antiulcer agent, a coronary vasodilator, a peripheral vasodilator, an antibiotic, an antibacterial agent, an antispasmodic, an antitussive, an antiasthmatic agent, a bronchodilator, a diuretic, a muscle relaxant, a brain metabolism improver, a tranquilizer, a β-blocker, an antiarrhythmic agent, a gout suppressant, an anticoagulant, an antiepileptic agent, an antihistaminic, an antiemetic, a hypotensive, a sympathomimetic agent, an expectorant, an oral antidiabetic agent, a circulatory agent, an iron preparation, a vitamin, a pollakiuria remedy, or an angiotensin-converting enzyme inhibitor.

21. A rapidly soluble tablet made in accordance with the method of claim 10.

22. A rapidly soluble tablet for oral administration of a therapeutic substance to a human or animal which comprises a kneaded wet compressed shaped tablet which comprises at least 93% by weight, based on the weight of the tablet, of a pharmaceutical additive which is rapidly soluble in water sufficient to form a rapidly soluble tablet and a therapeutically effective amount of a therapeutic substance, said tablet having been compression shaped with a compression force of from about 50 to about 1000 kg in a wet state and thereafter dried, said wet tablet containing from about 1 to about 3% by weight of water.

23. A rapidly soluble tablet for oral administration of a therapeutic substance to a human or animal which comprises a kneaded wet compressed shaped tablet which comprises an amount of a pharmaceutical additive which is rapidly soluble in water sufficient to form a rapidly soluble tablet and a therapeutically effective amount of a therapeutic substance, said tablet having been compression shaped with a compression force of from about 150 to about 1000 kg in a wet state and thereafter dried, said wet tablet containing from about 1 to about 10% by weight of water.

24. A process for the production of a rapidly soluble, glazed tablet for oral administration of a therapeutic substance to a human or animal, which comprises mixing a pharmaceutical additive which is rapidly soluble in water and a therapeutically effective amount of a therapeutic substance, adding and uniformly dispersing an amount of water of from about 1 to about 10% by weight of the wet tablet and sufficient to enable the mixture to be kneaded, kneading the mixture and while the kneaded mixture is wet, compression shaping it at a compression force of about 50 to about 1000 kg into tablet form, drying the tablet and glazing the outer surface thereof, whereby the tablets produced are rapidly soluble in the oral cavity of a human or animal upon administration.

25. The process of claim 24, wherein said glazing is effected by exposing the tablet to steam for at least one second.

26. A rapidly soluble tablet for oral administration of a therapeutic substance to a human or animal which comprises a kneaded wet compressed shaped tablet which comprises at least 93% by weight, based on the weight of the tablet, of a pharmaceutical additive which is rapidly soluble in water sufficient to form a rapidly soluble tablet and a therapeutically effective amount of a therapeutic substance, said tablet having been compression shaped with a compression force of from about 50 to about 1000 Kg in a wet state, with the wet tablet containing from about 1 to about 3% by weight of water, and thereafter drying the tablet and glazing the outer surface thereof, whereby the tablets produced are rapidly soluble in the oral cavity of a human or animal upon administration.

27. The rapidly soluble tablet of claim 26, wherein said glazing is effected by exposing the tablet to steam for at least one second.

28. The rapidly soluble tablet of claim 1, with said tablet having been compression shaped with a compression force of from about 150 to about 1000 kg in a wet state and thereafter dried.

* * * * *